(12) United States Patent
    Altman

(10) Patent No.: US 11,864,787 B2
(45) Date of Patent: Jan. 9, 2024

(54) THROMBECTOMY DEVICE AND METHODS OF USE

(71) Applicant: Sanford Altman, Miami, FL (US)

(72) Inventor: Sanford Altman, Miami, FL (US)

( * ) Notice: Subject to any disclaimer, the term of this patent is extended or adjusted under 35 U.S.C. 154(b) by 137 days.

(21) Appl. No.: 17/387,078

(22) Filed: Jul. 28, 2021

(65) Prior Publication Data

US 2023/0029532 A1    Feb. 2, 2023

(51) Int. Cl.
    *A61B 17/3205*    (2006.01)
    *A61B 17/3207*    (2006.01)
    *A61B 17/00*      (2006.01)

(52) U.S. Cl.
    CPC .. *A61B 17/32056* (2013.01); *A61B 17/32075* (2013.01); *A61B 17/320758* (2013.01); *A61B 2017/00867* (2013.01); *A61B 2017/320775* (2013.01)

(58) Field of Classification Search
    CPC . A61B 17/221; A61B 17/225; A61B 17/2202; A61B 17/3207; A61B 17/320758; A61F 2/01; A61F 2/013
    See application file for complete search history.

(56) References Cited

U.S. PATENT DOCUMENTS

| | | | |
|---|---|---|---|
| 5,383,887 A | 1/1995 | Nadal | |
| 6,221,006 B1 | 4/2001 | Dubrul et al. | |
| 6,635,070 B2 * | 10/2003 | Leeflang | A61B 17/22 606/200 |
| 6,676,682 B1 * | 1/2004 | Tsugita | A61F 2/013 606/200 |
| 6,945,977 B2 | 9/2005 | Demarais et al. | |
| 8,252,020 B2 | 8/2012 | Hauser et al. | |
| 8,956,386 B2 | 2/2015 | Hauser et al. | |
| 9,579,116 B1 | 2/2017 | Nguyen et al. | |
| 9,579,119 B2 | 2/2017 | Cully et al. | |
| 9,827,084 B2 | 11/2017 | Bonnette et al. | |
| 10,799,331 B2 | 10/2020 | Hauser | |
| 2007/0208370 A1 * | 9/2007 | Hauser | A61B 17/22012 606/200 |
| 2010/0185210 A1 | 7/2010 | Hauser et al. | |
| 2010/0268263 A1 | 10/2010 | Edelman et al. | |
| 2010/0268264 A1 | 10/2010 | Bonnette et al. | |
| 2014/0018840 A1 | 1/2014 | Morgan et al. | |
| 2017/0020555 A1 | 1/2017 | Ferrera et al. | |
| 2019/0046227 A1 | 2/2019 | Cully et al. | |
| 2019/0365397 A1 | 12/2019 | Bar | |
| 2020/0129282 A1 | 4/2020 | Hauser | |

FOREIGN PATENT DOCUMENTS

| | | |
|---|---|---|
| CN | 102970938 A | 3/2013 |
| CN | 111491580 A | 8/2020 |

* cited by examiner

*Primary Examiner* — Tuan V Nguyen
(74) *Attorney, Agent, or Firm* — SLEMAN & LUND LLP

(57) ABSTRACT

A thrombectomy system includes a frame having plurality of struts joined at an apex, a netting coupled to the plurality of struts, a pestle moveable relative to the frame and configured and arranged to macerate a clot within a vessel, adherent to its walls and against a portion of the apex of the frame.

16 Claims, 4 Drawing Sheets

THROMBECTOMY DEVICE AND METHODS OF USE

FIELD OF THE DISCLOSURE

Figure 1:
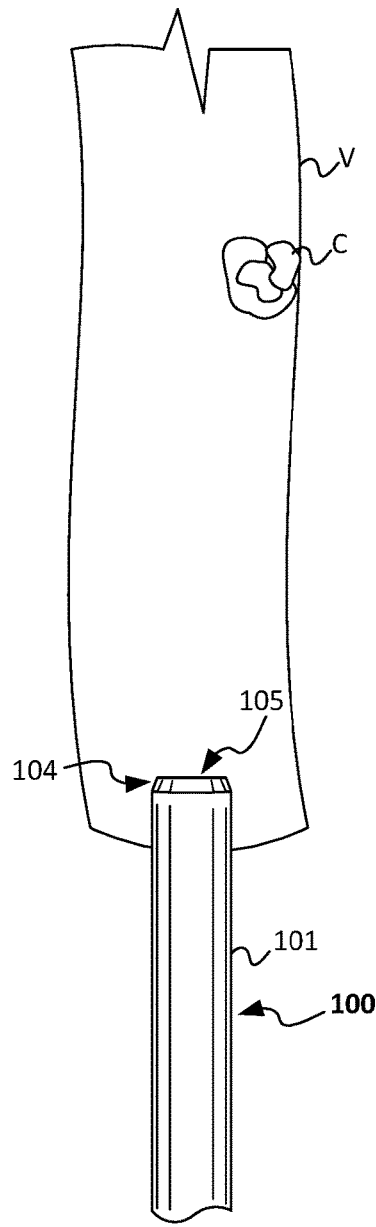

The present disclosure relates to thrombectomy devices and systems used in medical procedures. More particularly the present disclosure relates to clot-macerating thrombectomy devices and systems.

BACKGROUND OF THE DISCLOSURE

Clot formation in the vascular system occurs for a variety of reasons. Whether acute or chronic, clot within the vasculature is a concern. Methods to treat the clot vary from simple medical management to more aggressive thrombolytic, thromboaspiration and/or thrombectomy techniques. When clot removal from a vascular structure is desired, the goal is the same; to remove the clot in the simplest, safest and quickest manner. Currently, a variety of devices and techniques exist, none of which are perfect but all of which play a role in today's physician's armamentarium used to remove clot from the circulatory system.

Current thrombolytic techniques carry with them the risk of bleeding, which can be significant if not lethal. The risk of bleeding increases with increasing infusion times and dosing of thrombolytic agents. Thromboaspiration and thrombectomy devices come in an array of designs with some working better than others. Perhaps the greatest risk of any declotting procedure is the risk of clot dislodgement and distal migration. In the arterial bed, distal migration of clot can result in clot lodging in vascular structures converting a partial obstruction to a complete occlusion with resultant limb threatening ischemia. In the venous system, with slower flow and lower pressures, clot formation often results in large volumes of clot, which if embolized, can result in life threatening pulmonary embolism. Another area of frequent clot formation is in grafts and fistula used for hemodialysis some of which contain large volumes of clot, which if not managed properly can have serious, potentially lethal complications.

Thus, despite advances that have been made in this area, there are a variety of problems associated with currently available devices and methods. Hence, there is a continuing need for improved thrombectomy devices and methods to address at least some of these concerns.

SUMMARY OF THE DISCLOSURE

In some examples, a thrombectomy system includes a frame having a plurality of struts joined at an apex, a netting coupled to the plurality of struts, a pestle moveable relative to the frame and configured and arranged to macerate a clot against a portion of the apex of the frame.

BRIEF DESCRIPTION OF THE DISCLOSURE

Various embodiments of the presently disclosed thrombectomy systems are disclosed herein with reference to the drawings, wherein:

FIGS. 1-11 are schematic illustrations of the use of a thrombectomy device according to the present disclosure.

Various embodiments of the present invention will now be described with reference to the appended drawings. It is to be appreciated that these drawings depict only some embodiments which may or may not all be required for functionality of the invention and are therefore not to be considered limiting of its scope.

DETAILED DESCRIPTION

Despite the various improvements that have been made to thrombectomy devices, conventional devices suffer from some shortcomings as described above.

There therefore is a need for further improvements to the devices, systems, and methods of removing clots from the vasculature. Among other advantages, the present disclosure may address one or more of these critical needs.

As used herein, the term "proximal," when used in connection with a component of a thrombectomy system, refers to the end of the component closest to the physician, the patient and others when the thrombectomy system is inserted in a patient, whereas the term "distal," when used in connection with a component of a dilator, refers to the end of the component farthest from the thrombectomy system residing or intended to reside within the desired location. Likewise, the terms "trailing" and "leading" are to be taken as relative to the operator (e.g., physician) of the system. "Trailing" is to be understood as relatively close to the operator, and "leading" is to be understood as relatively farther away from the operator.

As shown in FIGS. 1-11, a blood vessel "V" may include thrombus or blood clots "C". While thrombus formation can be a healthy response to injury, it can also be harmful, where clot formation can reduce or obstruct blood through healthy or diseased blood vessels. In some instances, the thrombi adhere to the wall of a blood vessel as shown in FIG. 1. To safely remove the blood clot "C", a hollow sheath 100 can be inserted into the vessel near the site of the clot. Sheath 100 may extend between a proximal end (not shown) and distal end 104 and may include a lumen 105 for introducing the thrombectomy system as will be described below. Sheath 100 may include a body 101 formed of various materials including polymers (e.g., polyethylene terepthalate, polyethylene, high density polyethylene, polypropylene, polytetrafluoroethylene, expanded polytetrafluoroethylene, poly (ethylene-co-vinyl acetate), poly(butyl methacrylate), and co-polymers thereof) or other suitable materials known in the art.

Figure 2:
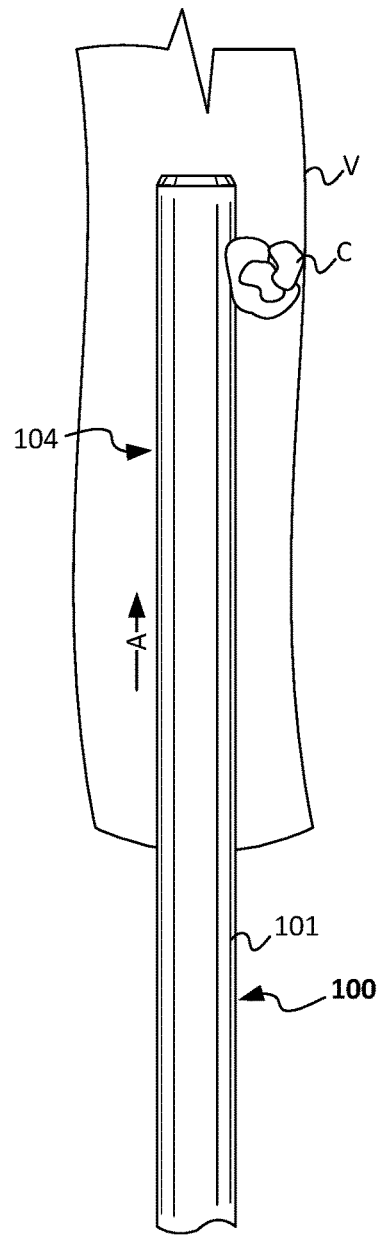
Figure 3:
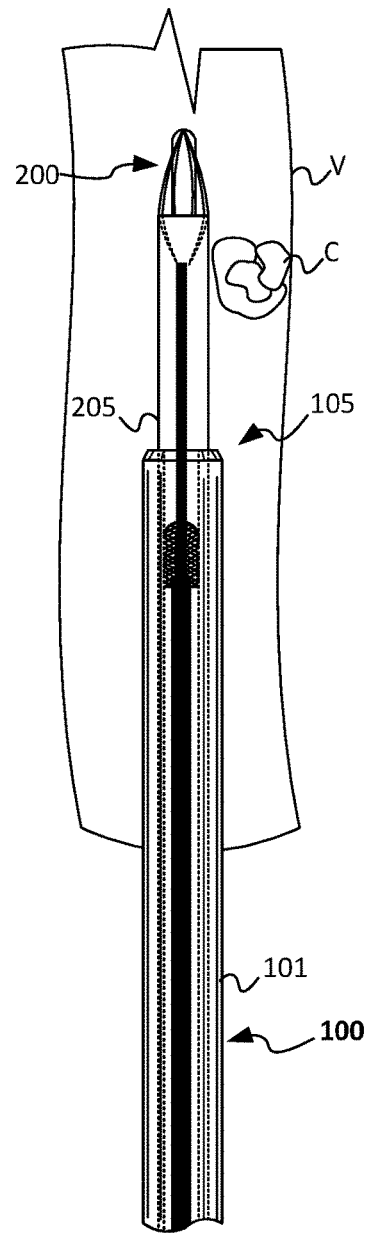

As shown in FIG. 2, sheath 100 may be advanced within the vessel "V" in the direction of arrow "A" to a site adjacent blood clot "C". In some examples, sheath 100 may be advanced over a standard wire with the distal end of the sheath being positioned adjacent to the desired location of the thrombectomy system. In some examples, the sheath 100 is initially advanced past the clot until the thrombectomy system is deployed (FIG. 2) and then retracted to bracket the clot (FIG. 3). Once the operator (e.g., physician) has determined that the device is properly in place relative to the clot, a thrombectomy system 200 may be advanced through lumen 105 of sheath 100. As shown in FIG. 3, in this initial delivery condition, thrombectomy system 200 includes a tubular catheter 205 collapsed to fit within and travel through sheath 100. In FIG. 3, the distal tip portions of the thrombectomy system are beginning to be deployed from catheter 205. Details of each of the components of thrombectomy system 200 will be appreciated with each successive figure that shows the operation of the device.

In one example, sheath 100 is advanced just distal to the clot and thrombectomy system 200 including catheter 205 is advanced through the sheath, past the blood clot "C" so that the clot is disposed between the distal end of the thrombectomy system, and the sheath 100. The sheath is then retracted slightly and components of the thrombectomy system 200 are deployed through catheter 205. As shown in the deployed state of FIG. 4, thrombectomy system 200 may extend between a proximal end (not shown), and a distal end 204. Thrombectomy system 200 may generally include a rigid frame 220, and a netting 230 to be deployed through catheter 205. In this example, a rigid or semi-rigid frame 220 is in the shape of a cone, cap, basket or "umbrella" to name a few, that includes a plurality of struts 222 coupled to an inner pusher rod 210 at one or more of the struts. Frame 220 may comprise a shape memory material that is configured to collapse within catheter 205 and to return to its expanded umbrella shape upon deployment from the catheter. In at least some examples, frame 220 is formed of a biocompatible polymer or metal, such as a shape memory alloy (e.g., Nitinol, etc.). Frame 220 may be configured as an umbrella and sized and/or shaped to fit within the blood vessel to prevent a large clot from migrating past the frame downstream through the blood vessel. When deployed through catheter 205, frame 220 may expand and abut the walls of the blood vessel, securing the vessel from any significant distal clot migration that could otherwise occur during a mechanical thrombectomy procedure.

In this example, a netting 230 is coupled to the rigid frame 220 and configured to cover the frame 220 to catch clots that travel into the frame. Other clot-trapping features or filters may be used instead of netting 230. Netting 230 may include a number of individual panels 232 coupled to the frame at terminal ends 224 of the frame. Alternatively, a single piece of netting may be used. In at least some examples, netting 230 is only coupled to the frame at the terminal ends (the proximal-most portions) and not at the apex 223 or the lengths of the struts, so that the frame can be inverted without inverting the netting as will be described in greater detail with reference to FIG. 9. Netting 230 may comprise braided metallic strands or polymeric or natural fibers.

In some examples, the pusher rod 210 may be opposed, locked into or coupled to the apex 223 of the frame 220 (e.g., a radially central region where at least some of the struts meet and/or the most distal end of the frame) and used to advance the frame and with it netting 230. Apex 223 and/or distal end of pusher 210 may form a substantially conical or flat surface that will be used as a mortar to grind the clot via pestle 250. In one example, a second control wire 212 may extend parallel with, or concentric with the pusher rod 210, the control wire 212 being configured and arranged to expand the frame from the fully collapsed condition to an expanded umbrella condition as shown in FIG. 4 or to invert the frame.

Figure 4:
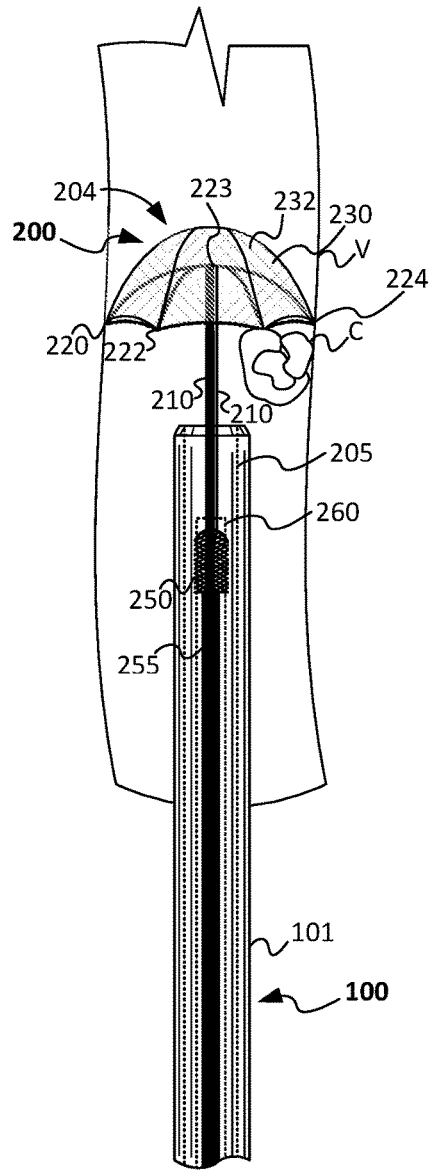
Figure 5:
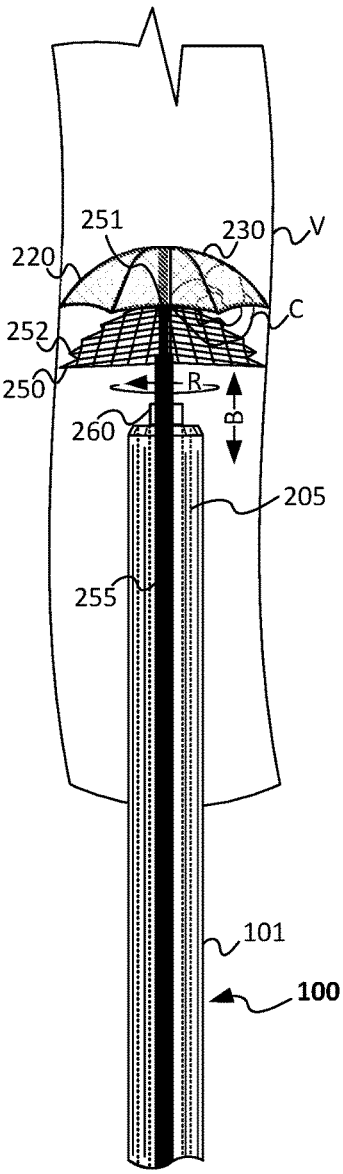

Still with reference to FIG. 4, a pestle 250 may also be introduced through lumen 105 of sheath 100 via sleeve 260 and advanced toward frame 220, the pestle 250 being coupled to a pestle shaft 255. With frame 220 and netting 230 in place, the pestle may be used to displace the clot "C" and push it into frame 220. Shaft 255 may be used to push pestle 250 out of the sheath. In at least some examples, shaft 255 may be hollow and configured to fit concentric with, or around, pusher rod 210 and be translatable relative thereto. In at least some examples, pestle 250 may be formed of a shape memory material and may be configured to fan out and return to the expanded condition shown in FIG. 5.

The shape of pestle 250 may be varied as desired. In some examples, pestle 250 may include a macerating and/or cutting rotational tip 251 its distal end along with a conical, diamond, flower, brush or other shaped macerating radially-extending features 252 designed to provide wall contact on the rotational portion of the device just proximal to its macerating/grinding tip. Pestle 250 is designed to macerate the intravascular clot, allow for vessel wall contact as well as macerate any clot trapped in the conical mortar umbrella frame. In at least some examples, pestle 250 and frame 220 have complementary shapes, and the pestle is configured to at least partially fit within the mortar frame.

The macerating/grinding tip 251 may "chew up" any clot present at the apex of the umbrella mortar frame at its central apex, a specifically designed macerating surface. The conical, diamond, flower or other-shaped radial portions of pestle 250 can be accomplished by using either a memory shaped wire which forms once the outer most sleeve 260 of this device is pulled back, or a multitude of attached graded fibers placed to create a desired conical, diamond, flower or other shaped effect again forming once the overlying outer sleeve 260 has been pulled back. Outer sleeve 260 may also serve as a thromboaspiration channel or port for administration of fluids or medications.

Once frame 220 (and with it netting 230) is in place and the pestle 250 has been exposed, mechanical thrombectomy is set to begin. Once activated the rotation of pestle 250 along with the inner macerator/grinder will be utilized to simultaneously macerate clot. A lumen of outer sleeve 260 may also be utilized to inject thrombolytic agents such as tPA, contrast agents to assess the effectiveness of: the thrombectomy and may also be used to aspirate the clot slurry present. Once has been determined that the clot has been macerated within its desired location, pestle 250 may be advanced all the way to the apex of the mortar umbrella. Pestle 250 may be translated back-and-forth along the longitudinal axis in the direction of arrows "B" to macerate the clot. Additionally, pestle 250 may be manually or mechanically rotated to aid in the maceration process as shown by arrow "R". Both the translation and the rotation may be accomplished by manipulating shaft 255 within sheath 100 with shaft of pestle 250 attached to a mechanical drive unit.

In the case of residual clot residing in frame 220, the pestle may be advanced all the way to the apex of the frame with its macerating surface of tip 251 serving as a macerating pad allowing the device to chew up any clot in its way, similar to a traditional mortar and pestle. This feature will help to break up any clot that the conical macerator could not completely treat. This is a common problem seen with most currently available mechanical thrombectomy devices where the device can provide clot maceration for some of the clot with other portions of the clot being more resilient to this technique. The central macerator on tip 251 may include blades or grinding coatings to allow it to bore through clot. As all the steps are performed "over the wire" the safety of this mechanism is assured as designed by one skilled in the art.

Figure 6:
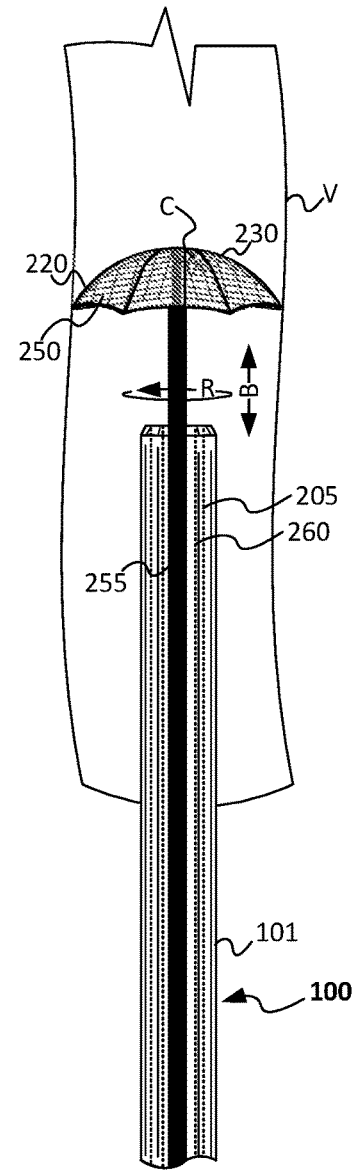
Figure 7:
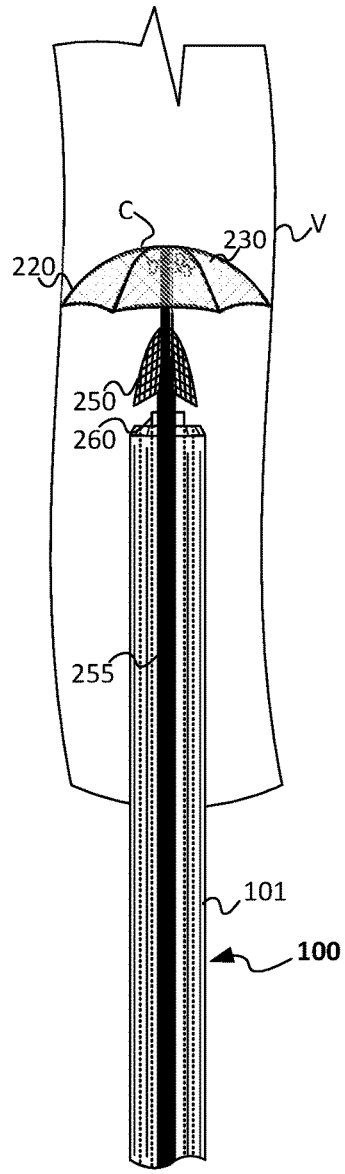

As shown in FIG. 6, this process of translating and rotating the shaft 255 to macerate with pestle 250 may continue until the clot "C" has been broken down into smaller fragments, some which are still retained or captured by netting 230, and others that are too fine, flowing downstream, the fine particles that are small enough to fit through the netting being too small to cause any significant harm.

Figure 8:
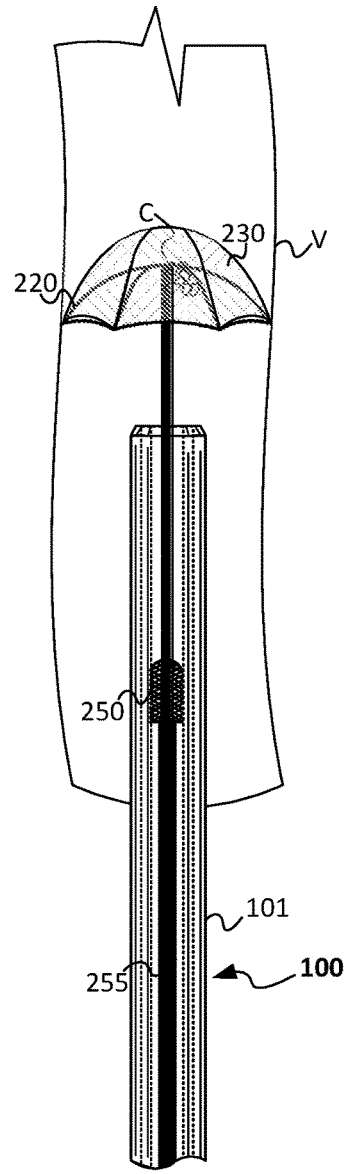
Figure 9:
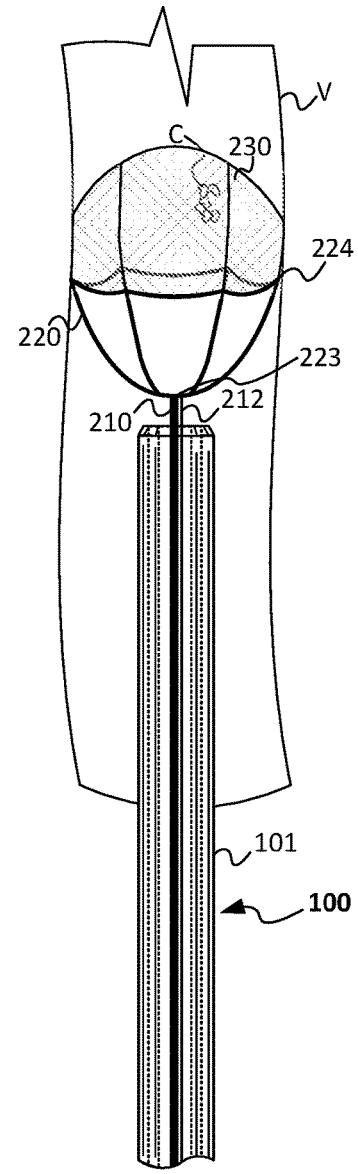
Figure 10:
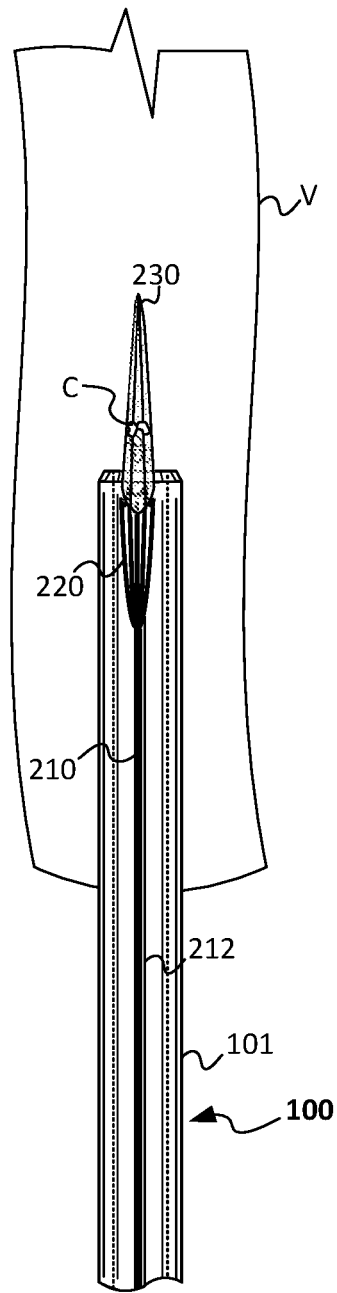
Figure 11:
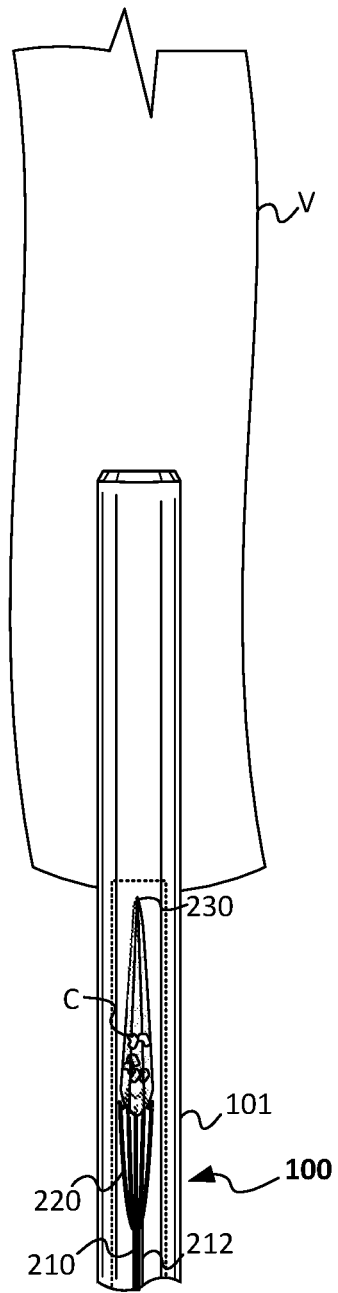

When the operator determines that the maceration process is sufficiently complete, the pestle 250 may be retracted back toward the sleeve 260 (FIG. 7), the clot still being contained by the netting 230. In FIG. 8, pestle 250 is shown been collapsed and retracted back into the sheath, where it will be removed through the proximal end. With the pestle 250 removed, the operator may then manipulate pusher rod 210 and control wire 212 to actuate the frame into the retrieval condition. In one example, the operator may hold pusher rod 210 in place while pulling on control wire 212 to invert frame 220 by pulling on the apex 223 of the frame. Other methods of inverting the frame 220 are also possible. In this example, clot "C" remains captured by netting 230 (FIG. 9) while the frame has been inverted, the netting being coupled to the terminal ends 224 of the frame.

The operator may then gently pull back on the pusher rod 210 and control wire 212 to further collapse the frame 220 and bring it within the lumen of the sheath (FIGS. 10-11), the netting 230 following thereafter with the clot "C" until the thrombectomy system 200 has been completely removed, followed by removal of sheath 100.

As will be appreciated, this multi-modality mechanical thrombectomy device and filter system is designed to provide effective clot maceration through a combination of thrombectomy techniques, with or without thromboaspiration, while providing additional safety through a clot catching-macerating surface retractable filter umbrella.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

What is claimed is:

1. A thrombectomy system comprising:
    a frame having a plurality of struts joined at an apex, the frame being configured and arranged to transition between (i) a collapsed condition, (ii) an expanded condition, and (iii) an inverted condition during removal;
    a netting coupled to the plurality of struts; and
    a pestle moveable relative to the frame and configured and arranged to macerate a clot against a portion of the apex of the frame.

2. The thrombectomy system of claim 1, wherein the expanded condition is umbrella-shaped.

3. The thrombectomy system of claim 1, wherein the frame is coupled to a pusher rod.

4. The thrombectomy system of claim 1, wherein the frame comprises a shape memory material.

5. The thrombectomy system of claim 1, wherein the netting is configured to cover the frame and is only attached to a plurality of proximal-most ends of the frame.

6. The thrombectomy system of claim 1, wherein the pestle includes a distal tip for macerating the clot and radially-extending features for contacting a wall of a blood vessel for maceration within the blood vessel, the pestle being rotatable relative to the frame.

7. The thrombectomy system of claim 1, wherein the pestle and the frame have complementary shapes, and the pestle is configured to at least partially fit within the frame.

8. The thrombectomy system of claim 1, further comprising a sheath having a lumen, the sheath being sized to receive the frame.

9. The thrombectomy system of claim 8, further comprising a catheter translatable relative to the sheath and configured and arranged to deliver the frame.

10. The thrombectomy system of claim 9, further comprising a sleeve translatable relative to the sheath and configured and arranged to deliver the pestle.

11. A thrombectomy system comprising:
    a frame having a plurality of struts joined at an apex;
    a netting coupled to the plurality of struts; and
    a pestle moveable relative to the frame and configured and arranged to macerate a clot against a portion of the apex of the frame, wherein the netting is coupled to the frame only at terminal ends of the frame.

12. A method of removing a blood clot from a blood vessel, comprising:
    providing a sheath within the blood vessel;
    providing a frame having a plurality of struts joined at an apex, a netting coupled to the plurality of struts, and a pestle moveable relative to the frame and configured and arranged to macerate a clot against a portion of the apex of the frame;
    deploying each of the frame, the netting and the pestle through the sheath; and
    pressing the pestle against the apex of the frame to macerate the blood clot.

13. The method of removing a blood clot of claim 12, wherein deploying each of the frame, the netting and the pestle through the sheath comprises deploying the frame through the sheath and transitioning the frame between a collapsed condition and an expanded umbrella condition.

14. The method of removing a blood clot of claim 12, further comprising using the pestle to dislodge the blood clot and decouple it from a blood vessel wall.

15. The method of removing a blood clot of claim 12, further comprising removing, in order, the pestle, the frame, the netting and the sheath from the blood vessel.

16. A method of removing a blood clot from a blood vessel, comprising:
    providing a sheath within the blood vessel;
    providing a frame having a plurality of struts joined at an apex, a netting coupled to the plurality of struts, and a pestle moveable relative to the frame and configured and arranged to macerate a clot against a portion of the apex of the frame;
    deploying each of the frame, the netting and the pestle through the sheath; and
    transitioning the frame to an inverted condition for removal.

* * * * *